United States Patent [19] [11] 4,017,564
Arend et al. [45] Apr. 12, 1977

[54] PROCESS FOR THE PRODUCTION OF (METH)ALLYL PHOSPHONIC ACID DIALKYL ESTERS

[75] Inventors: Günter Arend; Heinz Schaffner; Jürgen Schramm, all of Dormagen, Germany

[73] Assignee: Bayer Aktiengesellschaft, Leverkusen, Germany

[22] Filed: Aug. 26, 1975

[21] Appl. No.: 607,946

[30] Foreign Application Priority Data

Sept. 5, 1974 Germany .......................... 2442428

[52] U.S. Cl. .............................................. 260/969
[51] Int. Cl.$^2$ ........................................... C07F 9/40
[58] Field of Search .................................... 260/969

[56] References Cited

UNITED STATES PATENTS 2,636,027   4/1953   Coover et al. ................. 260/956 X
3,493,639   2/1970   Tavs ................................. 260/969
3,705,214   12/1972  Martin ............................. 260/969

FOREIGN PATENTS OR APPLICATIONS 1,810,431   6/1970   Germany
48-75528    11/1973  Japan

OTHER PUBLICATIONS

Arbusov et al., Izvest. Akad. Nauk. SSSR, Otdel Khim. Nauk (1951), p. 714.
Skwarski et al., Zesz. Nauk. Politech. Lodz, Wlok, 16 (1967) pp. 55–71.

Primary Examiner—Richard L. Raymond
Attorney, Agent, or Firm—Plumley and Tyner

[57] ABSTRACT

The invention relates to a process for the production of allyl or methallyl phosphonic acid dialkyl esters by reacting allyl chloride or methallyl chloride with trialkyl phosphites at temperatures of from 80° to 160° C in the presence of a compound of avalent and/or monovalent nickel or in the presence of a compound of avalent, monovalent or divalent cobalt.

8 Claims, No Drawings

PROCESS FOR THE PRODUCTION OF (METH)ALLYL PHOSPHONIC ACID DIALKYL ESTERS phosphonic This invention relates to an improved process for the production of allyl or methallyl phophonic acid dialkyl esters from allyl or methallyl chloride.

It is known that (meth)allyl phosphonic acid dialkyl esters can be obtained by the Michaelis-Becker reaction from (meth)allyl halides and sodium dialkyl phosphite. Unfortunately, this process gives only a poor yield and is accompanied by undesirable secondary reactions, cf. K. Sasse in: Houben-Weyl, Methoden der Organischen Chemie, 4th Edition, Vol. 12/1, pages 446 et seq. It is also known that (meth)allyl phosphonic acid dialkyl esters can be obtained from allyl bromide by the Michaelis-Arbusow reaction, cf. U.S. Pat. No. 2,636,027 and A.E. Arbusow et al., Izvest. Akad. Nauk. SSSR, Otdel, Khim. Nauk 1951, 714. This process is costly because expensive allyl bromide has to be used and because the alkyl bromide formed has to be worked up.

Hitherto, it has only been possible to carry out the Michaelis-Arbusow reaction using allyl or methallyl chloride, an inexpensive, readily available material, with moderate yields under rigorous reaction conditions in the absence of a catalyst. Thus, it is not possible to obtain any reaction between allyl chloride and triethyl phophite at normal pressure. Where the reaction is carried out under pressure, the yield obtained using a 10-molar excess of allyl chloride amounts to at most 53% according to A. E. Arbusow et al., Izvest. Akad. Nauk. SSSR, Otdel. Khim, Nauk. 1951, 714. Other authors do not quote any yield at all (Zesz. Nauk. Politech. Lodz, Wlok 16, 55–71 (1967).

According to Japanese patent specification Sho-48-75 528, (meth)allyl halides are reacted with trialkyl phosphites in the presence of compounds of divalent nickel to form (meth)allyl phosphonic acid dialkyl esters. The yields obtained from this reaction, as determined by gas chromatography, amount at best to 90% of the theoretical.

According to DOS No. 1,810,431, vinyl chloride is reacted with trialkyl phosphites in the presence of nickel halides to form vinyl phophonic acid dialkyl esters. This reaction also has to be catalysed. Our own tests have shown that Raney nickel and compounds of avalent and/or monovalent nickel, such as for example nickel tetracarbonyl or $\pi$-allyl nickel chloride, do not catalyse this reaction.

In contrast with these results, it has surprisingly been found that Raney nickel and compounds of avalent and/or monovalent nickel catalyse the reaction of allyl and methallyl chlorides to form the corresponding phosphonic esters much more effectively than compounds of divalent nickel. The catalytic activity of Raney nickel and of nickel-O- and nickel-I-compounds in the Michaelis-Arbusow reaction is limited to halides of allyl structure, i.e. the corresponding reactions of alkyl, vinyl and aryl halides cannot be catalysed by these compounds.

Accordingly, it is an object of the present invention to provide a process for the production of allyl and methallyl phosphonic acid alkyl esters.

It is a further object of this invention to improve the yield of such esters in a process for the production thereof. These and other objects, which will be evident from the description and the examples are accomplished by a process for the production of allyl and methallyl phosphonic acid dialkyl esters corresponding to the general formula

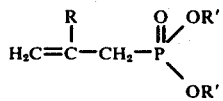

wherein
R represents hydrogen or methyl, and
R' represents a straight-chain or branched, optionally halogen-substituted alkyl radical having up to 4 carbon atoms, which comprises reacting allyl chloride or methallyl chloride with a phosphorus acid trialkyl ester (trialkyl phosphites) corresponding to the formula:

in which R' is as defined above, under atmospheric pressure at a temperature in the range of from 80° to 160° C in the presence of a catalyst being selected from the group consisting of elemental nickel, a compound of avalent nickel, a compound of monovalent nickel, a mixture of compounds of avalent and monovalent nickel, a compound of avalent cobalt, a compound of monovalent cobalt and a compound of divalent cobalt.

The catalyst is generally used in a quantity of from 0.1 to 7 mol % and preferably in a quantity of from 0.2 to 5 mol % based on the trialkyl phosphite. The reaction is preferably carried out at temperatures in the range of from 90° to 150° C.

Particularly suitable catalysts are, for example, finely divided nickel metal such as Raney nickel, nickel tetracarbonyl, nickel triphenyl phosphine tricarbonyl, nickel-bis-(triphenyl phosphine)-dicarbonyl, $\pi$-allyl nickel chloride, $\pi$-allyl nickel bromide, $\pi$-allyl nickel iodide, $\pi$-cycopentadienyl nickel nitrosyl and nickel diacrylonitrile.

Somewhat less effective but nevertheless equally suitable catalysts are, for example, Raney cobalt, dicobalt octacarbonyl, cobalt-II-chloride and cobalt-II-bromide.

Other elements adjacent to nickel and cobalt in the Periodic System, and compounds thereof, are catalytically inactive.

The reaction according to the invention is generally carried out by gradually adding the allyl or methallyl chloride to a mixture of the catalyst with the trialkyl phosphite at a temperature of from 80° to 160° C, preferably from 90° to 150° C, in the presence of a suitable polymerisation inhibitor. The reactions are only slightly exothermic, so no difficulties are involved in controlling the reaction temperature. The alkyl chloride formed, which depends on the type of trialkyl phosphite used, is distilled off through a short column during the reaction. A reflux condenser kept by cooling water to between 15° and 20° C is advantageously used as the column for preparing the phosphonic acid methyl and ethyl ester. The reaction is over when no more alkyl chloride distils off. The catalyst is optionally separated by filtration and the allyl phosphonic ester or methallyl phosphonic ester formed is purified by rectification.

One particular advantage of the process according to the invention is that the reaction between the trialkyl phosphite and allyl chloride (boiling point 45° C) or methallyl chloride (boiling point 72° C) can be carried out at atmospheric pressure. Although the reaction can be carried out under pressure, the yields obtained in that case are generally lower than those obtained where the reaction is carried out in the absence of excess pressure.

It is best to use a small excess of up to about 10 mol % of the chloride component because small quantities of the allyl or methallyl chloride used are entrained especially when methyl or ethyl chloride formed is distilled off. In general, the use of a larger excess of one of the two components actually has an adverse effect. In the presence of the catalysts according to the invention, the reaction takes place very quickly and is over after all the (meth)allyl chloride has been added. In general, there is no need for an after reaction. By contrast, much longer reaction times are required in cases where nickel-II-salts, of the type described in Japanese Patent Specification Sho-48-75 528, are used as catalysts. In that case, the reaction mixture has to be left reacting for between two and five hours after all the (meth)allyl chloride has been added.

The yields obtained where the nickel-O- and nickel-I-catalysts according to the invention are used are distinctly better than those obtained in cases where nickel-II-salts are used. According to Example 9 of Japanese Patent Specification Sho-48-75 528 for example, a yield of 90% of allyl phophonic acid diethyl ester, as determined by gas chromatography is obtained from the reaction of allyl chloride with triethyl phosphite using 2 mol % of $NiBr_2$ after a reaction time of 8 hours at 80° to 120° C. If, by contast, only 0.5 mol % of nickel tetracarbonyl are used as catalyst, an isolated yield of 90% of allyl phosphonic acid diethyl ester is obtained after a reaction time of 2 hours at 115° C. If the reaction is carried out under comparable conditions, at least 0.5 mol % of the nickel-O- or -I-compounds or at least 1.0 mol % of the nickel-II-salts are required. The yields obtained where the catalysts according to the invention are used are generally higher than those obtained where the nickel-II-salt catalysts are used cf. Examples 2 to 10 with Examples 13 to 21.

Another advantage of the process according to the invention is that the distillation sump can be reused as a catalyst, irrespective of the catalyst originally used. Thus, in one case, the distillation sump from the Raney-nickel-catalysed preparation of allyl phosphonic acid diethyl ester was stored for 4 weeks and was subsequently used as catalyst in another 10 successive reactions. Despite being used 10 times, the catalyst did not show any sign of reduction in activity.

The distillation sumps from the nickel-II-salt-catalysed reaction can also be reused as catalysts. Even after repeated use, the nickel-O- and nickel -I-catalysts still show greater catalytic activity than the nickel-II-catalysts.

In the case of relatively small reaction mixtures, there is no need to add a polymerisation inhibitor. In the case of relatively large reaction mixtures, however, it is advisable to add a stabiliser. Suitable stabilisers are, for example, hydroquinone, hydroquinone monomethyl ether, hydroquinone dimethyl ether, 2,6-di-t-butyl-p-cresol, pyrocatechol, 4-t-butyl pyrocatechol, phenothiazine or 4-hydroxy diphenyl amine. These stabilisers are preferably added to the reaction mixture in quantities of up to 2% by weight, based on (meth)allyl chloride.

On account of the ready oxidisability of the trialkyl phosphites, it is advantageous, although not essential, to carry out the reaction in a suitable inert gas atmosphere. Suitable inert gases are, for example, hydrogen, helium, nitrogen, argon and carbon dioxide.

The reaction may be carried out in an inert diluent, such as benzene, toluene, xylene, chlorobenzene, benzonitrile, methyl cyclohexane, petrol, dioxan or cyclohexanone. However, no particular advantages are obtained by using a solvent.

In one preferred embodiment of the process according to the invention, from 0.5 to 5 mol % of anhydrous Raney nickel is used as catalyst. The Raney nickel used must be highly reactive. Raney nickel which has aged or which, for example, has been stored for 2 days in benzene, toluene or xylene, is catalytically inactive. For further activation, it is advisable in many cases to pretreat the Raney nickel with the trialkyl phosphite for 1 to 2 hours at 140° to 150° C and in this way to activate it. All or some of the Raney nickel enters into solution. However, this solubility is by no means an adequate criterion of catalytic activity, because deactivated Raney nickel is also partly dissolved in the trialkyl phosphite under the above-mentioned conditions.

Following activation, addition of the (meth)allyl chloride is commenced, preferably at a temperature of from 120° to 150° C, after which the formation of alkyl chloride begins immediately. Once the reaction has started, the temperature can be lowered to around 100° C. After cooling, any undissolved Raney nickel still present is optionally filtered off and the phosphonic ester formed is distilled in vacuo through a column. This procedure is also advantageous where Raney cobalt is used as catalyst. The sump left may be repeatedly used as a catalyst without any reduction in yield. There is no need for thermal pretreatment with the trialkyl phosphite.

In another preferred embodiment of the process according to the invention, a solution of 0.2 to 1.0 mol % of nickel tetracarbonyl or $\pi$-allyl nickel chloride in the trialkyl phosphite is used. The (meth)allyl chloride is added dropwise at 120° to 140° C, the alkyl chloride formed distilling off through a column. The reaction is over immediately on completion of the dropwise addition and the (meth)allyl phosphonic ester formed is isolated in vacuo by fractional distillation. The sump left may be repeatedly used as a catalyst without any reduction in yield.

The reaction may also be advantageously carried out in this way where the other nickel and cobalt catalysts are used.

The allyl and methallyl phosphonic acid dialkyl esters produced in accordance with the invention are valuable monomers and comonomers for the production of substantially non-inflammable (co)polymers. They may be polymerised, for example, in a wide range of proportions with acrylonitrile, vinyl and vinylidene halides, such as vinyl chloride, vinyl bromide and vinylidene chloride, styrene and/or butadiene to form substantially non-inflammable copolymers of the type described, for example, in U.S. Pat. Nos. 2,636,027 and 2,827,475.

They also constitute readily obtainable intermediate products for chemical reactions, for example to form epoxides, diols, diene and halogen adducts, some of which show interesting physiological effects or may be used, for example, as flameproofing agents.

The invention is further illustrated but not limited by the following Examples in which the parts quoted are parts by weight.

Examples 2 to 12, 22 to 26, 33 to 35 and 37 to 42 illustrate the application of the process in accordance with the invention. Example 1 shows that, under the conditions of the process according to the invention, no yield is obtained in the absence of a catalyst. Comparison of Examples 2 to 12 with Examples 13 to 21, comparison of Example 23 with Example 24 and comparison of Examples 34 and 35 with Example 36 demonstrate the superiority of the catalysts according to the invention to the nickel-II-salts.

Examples 27 to 32 show that other transition metal compounds do not catalyse the Michaelis-Arbusow reaction of (meth)allyl chloride. Examples 43 and 44 show that the catalysts according to the invention are inactive in the Michaelis-Arbusow reaction of chlorides without an allyl structure.

EXAMPLES 1 to 12

Allyl phosphonic acid diethyl ester

The catalyst (quantities indicated in the following Table) and two parts of hydroquinone or phenothiazine are added to 322 parts of triethyl phosphite under a nitrogen atmosphere. After heating to 130° C, 160 parts of allyl chloride are added dropwise at 110° to 140° C. A vigorous evolution of ethyl chloride begins, whilst the unreacted fraction of the allyl chloride is condensed in the preceding water-cooled reflux condenser. The reaction is over when no more ethyl chloride distils off. The ethyl chloride given off is condensed in a condenser cooled with brine to approximately $-20°$ C and weighed, the yield generally being quantitative.

After cooling, the product is distilled through a column. Bp: 93°-96° C/10 Torr, $n_D^{20}$: 1.4328 to 1.4332. According to analysis by gas chromatography, the product has a purity of from 96 to 99%.

The reaction time is taken to be the total period of time elapsing from the beginning of the addition of allyl chloride to the end of the evolution of ethyl chloride in a 2-molar reaction mixture. The fraction with refractive index $n_D^{20}$ of from 1.4328 to 1.4332 was counted as the yield.

EXAMPLES 13 TO 21

Similar procedure for comparison with Examples 1 to 12:

| Example | Catalyst | Temp/Reaction time | Isolated yield |
|---|---|---|---|
| 13 | 0.2 mol % NiCl$_2$ | 130– 90° C/2 hours | 23.8 % |
| 14 | 0.5 mol % NiCl$_2$ | 130 ° C/2 hours | 59.5 % |
| 15 | 1.0 mol % NiCl$_2$ | 120° C/3 hours | 70 % |
| 16 | 1.5 mol % NiCl$_2$ | 130° C/2 hours | 76.5 % |
| 17 | 3.0 mol % NiCl$_2$ | 120° C/3 hours | 82 % |
| 18 | 0.2 mol % NiBr$_2$ | 130– 90° C/2 hours | none |
| 19 | 0.5 mol % NiBr$_2$ | 130– 90° C/2 hours | 25.8 % |
| 20 | 1.0 mol % NiBr$_2$ | 130° C/2 hours | 73.0 % |
| 21 | 1.5 mol % NiBr$_2$ | 130–135° C/2 hours | 79.5 % |

EXAMPLE 22

Preparation of allyl phosphonic acid diethyl ester with Raney nickel as catalyst In a flask flushed with nitrogen, 166 parts of triethyl phosphite, 0.5 part of hydroquinone and 2 parts (3.4 mol %), based on the phosphite, of highly active Raney nickel freshly decanted with ethanol and toluene are heated for 1 hour to 140° C, most of the nickel entering into solution. The dropwise addition of 80 parts by weight of allyl chloride is commenced at 140° C. A vigorous evolution of ethyl chloride begins immediately and the reaction temperature is reduced to between 110° and 120° C. Shortly after the dropwise addition of the allyl chloride has been completed, the evolution of ethyl chloride is also over. The reaction mixture is allowed to cool and is then fractionated in vacuo. Yield 86 to 92% of the theoretical. Purity according to GC analysis: 97–98%.

EXAMPLE 23

The distillation sump from Example 22 is used as a catalyst for an equimolar mixture. The procedure is the same as in Examples 1 to 12. Yield: 90 to 95% of the theoretical, purity according to GC-analysis: 97–98%.

The distillation sump left may be reused as catalyst, even after 4 weeks' storage, without any reduction in yield or purity. Even after the catalyst had been used 10 times, it is not possible to detect any reduction in its activity.

| Example | Catalyst | Temp./Reaction time | Isolated yield |
|---|---|---|---|
| 1 | none | 120° C/7 hours | none |
| 2 | 0.2 mol % Ni(CO)$_4$ | 110 – 120° C/2 hours | 51 % |
| 3 | 0.5 mol % Ni(CO)$_4$ | 110 – 120° C/2 hours | 90 % |
| 4 | 1.0 mol % Ni(CO)$_4$ | 130 – 140° C/1 hour | 84 % |
| 5 | 1.5 mol % Ni(CO)$_4$ | 125° C/1 hour | 85 % |
| 6 | 0.2 val % π-allyl-nickel chloride* | 130 – 90° C/3.5 hours | 14.3 % |
| 7 | 0.5 val % π-allyl-nickel chloride* | 140° C /2 hours | 80.3 % |
| 8 | 1.0 val % π-allyl-nickel chloride* | 135 – 140° C/1 hour | 80.5 % |
| 9 | 1.5 val % π-allyl-nickel chloride* | 130 – 135° C/1.5 hours | 84.5 % |
| 10 | 3.0 val % π-allyl-nickel chloride | 110° C/1 hour | 94.0 % |
| 11 | 2.0 mol % Ni-triphenyl phosphine tricarbonyl | 125° C/1 hour | 95.5 % |
| 12 | 3.0 mol % Ni-di-acrylonitrile | 125° C/2 hours | 78 % |

*based on equivalents of Ni

EXAMPLE 24

This test is a repetition of test 17. The distillation sump from Example 17 was used as catalyst. Yield: 83% of the theoretical.

Comparison of Example 23 with Example 24 again shows the greater catalytic activity of nickel-O- and nickel-I-derivatives compared with nickel-II-compounds, even when the distillation sump is reused as a catalyst.

EXAMPLES 25 TO 32

Allyl phosphonic acid diethyl ester, catalysts tests with different metal compounds. The procedure was as in Examples 1 to 12.

| Example | Catalyst | Temp./Reaction time | Yield |
|---|---|---|---|
| 25 | 3.0 mol % $CoCl_2$ | 120° C/3 hours | 85 % |
| 26 | 0.8 mol % $Co_2(Co)_8$ ($\hat{=}$ 1.6 val % Co) | 150 – 160° C/18 hours | 75 % |
| 27 | 1.1 mol % $PdCl_2$ | 120° C/3 hours | 0 % |
| 28 | 3.0 mol % $HgCl_2$ | 125° C/3 hours | 0 % |
| 29 | 2.0 mol % $CuBr_2$ | 120° C/5 hours | 0 % |
| 30 | 2.0 mol % $FeCl_3$ | 120° C/5 hours | 0 % |
| 31 | 2.0 mol % $Ag(O_2C-CH_3)_2$ | 130° C/5 hours | 0 % |
| 32 | 1.0 mol % $Fe(Co)_5$ | 140° C/5 hours | 0 % |

Examples 26 and 25 demonstrate the catalytic activity of dicobalt octacarbonyl and of cobalt-II-chloride (for Raney nickel, cf. Example 33). Examples 27 to 32 show that elements adjacent to nickel and cobalt in the Chemical Periodic System, in the form of their salts or carbonyls, do not have any catalytic activity.

EXAMPLE 33

166 parts of triethyl phosphite are heated for 1 hour to 140° C in a nitrogen atmosphere with 2 parts of highly active Raney cobalt (Ra-Co-Lu). A mixture of 1 part of phenothiazine and 80 parts of allyl chloride is then added dropwise at 140° C. Once the reaction has started, the temperature may be lowered to 120° C. After 5.5 hours, 63 parts of ethyl chloride have distilled off and the mixture is deep blue in colour. Fractional distillation gives 135 parts of allyl phosphonic acid diethyl ester, corresponding to 76% of the theoretical yield.

EXAMPLES 34 TO 36

Preparation of allyl phosphonic acid dipropyl ester from allyl chloride and tripropyl phosphite

| Example | Temp. °C | Catalyst | Molar ratio of allyl chloride to tripropyl phosphite | Yield % | Procedure |
|---|---|---|---|---|---|
| 34 | 140 | 1.4 mol % Raney-nickel | 1.2 : 1 | 86 | as in Example 22 |
| 35 | 140 | 1.5 mol % $Ni(CO)_4$ | 1.2 : 1 | 85 | as in Example 5 |
| 36 | 140 | 3 mol % $NiCl_2$ | 1.5 : 1 | 62 | as in Example 16 |

The yields relate to 5-molar mixtures.

Boiling point: 120° C/14 mm   $n_D^{20}$: 1.4352 – 1.4356
103° C/4 mm

Purity according to GC: 94 – 96%

Examples 36 again demonstrates the inferiority of $NiCl_2$ as catalyst compared with Raney nickel and nickel tetracarbonyl, despite the higher concentration of $NiCl_2$.

EXAMPLES 37 TO 38

Preparation of methallyl phosphonic acid diethyl ester from methallyl chloride and triethyl phosphite.

| Example | Temp °C | Catalyst | Molar ratio of methallyl chloride to triethyl phosphite | Yield % | Procedure |
|---|---|---|---|---|---|
| 37 | 110–140 | 1.5 mol % Raney-nickel | 1.1 : 1 | 79 | as in Example 22 |
| 38 | 130–140 | 2.0 mol % $Ni(CO)_4$ | 1 : 1.5 | 65 | as in Example 5 |

The yields relate to 5-molar mixtures. Boiling point: 104°–105° C/12 mm $n_D^{20}$: 1.4353–1.4363; Purity according to GC: 96–98%

EXAMPLE 39

Preparation of methallyl phosphonic acid-di-n-propyl ester from methallyl chloride and tri-n-propyl phosphite.

Following the procedure of Example 22, the following components are reacted at a temperature of 110° to 140° C:

208 parts of tri-n-propyl phosphite
80 parts of methallyl chloride
90 g of highly active Raney nickel ($\hat{=}$ 1.5 mol %)
1 part of phenothiazine The yield from a 30-molar reaction mixture amounts to 80% of the theoretical. Bp: 115°–122° C/12 mm;

$n_D^{20}$: 1.4377 Purity according to gas chromatography: 99%

| Analysis | C | H | P |
|---|---|---|---|
| calculated: | 54.5% | 9.6% | 14.1% |
| found: | 54.4% | 11.1% | 14.7% |

EXAMPLE 40

Preparation of methallyl phosphonic acid diisopropyl ester 208 parts of triisopropyl phosphite, 1.5 parts of phenothiazine and 3.4 parts of $Ni(CO)_4$ (corresponding to 2 mol %, based on the phosphite) are heated to 120°–130° C in a nitrogen atmosphere. 99 parts (corresponding to a 10% excess) of methallyl chloride are added dropwise over a period of 5 hours. 68 parts of isopropyl chloride (Bp: 35°–36° C) are distilled off through a column. The product is fractionated in vacuo through a column. Boiling point: 58°–63° C/0.25 Torr; Yield: 155 parts (70.5% of the theoretical): $n_D^{20}$: 1.4312 Purity according to GC: 97.3%

| Analysis | C % | H % | P % |
|---|---|---|---|
| calculated: | 54.5 | 9.6 | 14.1 |
| found: | 54.6 | 9.4 | 14.3 |

EXAMPLE 41

Preparation of allyl phosphonic acid dimethyl ester 124 parts of trimethyl phosphite, together with 1 part of Raney nickel, are heated for 1 hour to 130°–140° C in a nitrogen atmosphere. 80 parts of allyl chloride are then slowly added dropwise so that the temperature does not fall below 80° to 90° C. The methyl chloride formed escapes through the reflux condenser. The reaction is over after 22 hours. The Raney nickel is filtered off, followed by fractionation in vacuo. Bp: 83°–84° C/12 Torr; $n_D^{20}$: 1.4371; Yield: 86 parts, corresponding to 57% of the theoretical.

EXAMPLE 42

Allyl phosphonic acid-bis-(2-chloroethyl)-ester 270 parts of tris-(2-chloroethyl)-phosphite and 2 parts of Raney nickel are heated for 1 hour to 110°–120° C in a nitrogen atmosphere. 120 parts of allyl chloride are slowly added dropwise at that temperature so that the temperature always remains below 120° C. A mixture of allyl chloride and ethylene chloride distills off through a column at a head temperature of approximately 60° C.

The product is distilled off under a water jet vacuum at a sump temperature of 125° C, giving 280 parts of crude product, $n_D^{20}$: 1.4854. The crude product is stabilised with 2 parts of phenothiazine and fractionated in vacuo. Bp: 128°–129° C/0.4–0.6 Torr, $n_D^{20}$: 1.4800; Yield: 94 parts, corresponding to 38% of the theoretical.

Comparison Example 43

Catalytic inactivity of Ni-O- and Ni-I-compounds in the Arbusow reaction of vinyl chloride.

a. Raney nickel 500 parts of tri-n-propyl phosphite are added in a nitrogen atmosphere to 10 parts of highly active Raney nickel freshly washed with ethanol and benzene, followed by gradual heating to 150° C. 5 parts of the Raney nickel enter into solution.

5 parts of hydroquinone and 225 parts of liquid vinyl chloride are added to this mixture, followed by heating in an autoclave for 3 hours to 180° C. The tri-n-propyl phosphite is recovered intact after distillation, i.e. it did not react into vinyl phosphonic acid di-n-propyl ester.

b. π - Allyl nickel chloride

A mixture of 225 parts of vinyl chloride, 500 parts of tri-n-propyl phosphite, 5 parts of hydroquinone and 7.0 parts (1.6 mol %) of π-allyl nickel chloride is heated for 3 hours to 180° C in an autoclave. There is no reaction to form vinyl phosphonic acid di-n-propyl ester.

c. Nickel tetracarbonyl

A mixture of 250 parts of tri-n-propyl phosphite, 113 parts of vinyl chloride, 3 parts of hydroquinone and 3 parts of nickel tetracarbonyl is heated for 3 hours to 180° C in an autoclave. The tri-n-propyl phosphite is recovered intact after distillation, i.e. there was no reaction.

d. with $NiCl_2$ according to DOS No. 1.810,431

A mixture of 500 parts of tri-n-propyl phosphite, 9 parts of $NiCl_2$ (2.9 mol %), 2.4 parts of pyrocatechol and 300 parts of vinyl chloride is heated for 3 hours to 180° C in an autoclave. Fractionation through a column gives 325 parts (71%) of vinyl phosphonic acid-di-n-propyl ester.

This Example shows that the catalysts Raney nickel, π-allyl nickel chloride and nickel tetracarbonyl, which are eminently suitable for the reaction of (meth)allyl chloride with phosphites, are inactive in the corresponding reaction with vinyl chloride.

It can be seen from Examples 2 to 11, 22 and 24, 34, 35 and 37 to 42 that the catalysts used in accordance with the invention have no catalytic effect on the Michaelis-Arbusow reaction of alkyl chlorides, such as methyl, ethyl, propyl and isopropyl chloride. Example 44 shows that these catalysts do not have any activity, even in cases where alkyl halides with activating substituents in the β-position are used.

EXAMPLE 44 a. 270 parts of acetic acid-2-chloroethyl ester are slowly added dropwise at 130° to 150° C to a mixture of 166 parts of triethyl phosphite and 2.5 parts of nickel tetracarbonyl. There is no reaction.

b. The procedure is as in Example 44(a), except that 111 parts of epichlorhydrin are used instead of the acetic acid-2-chloroethyl ester. There is no reaction. $NiCl_2$ does not catalyse this reaction either.

c. The procedure is as in Example 44(a), except that 197 parts of β-chloropropionitrile are used instead of the acetic acid-2-chloroethyl ester. 16% of the corresponding phosphonic ester are obtained after a reaction time of 10 hours at 150° C. However, this quantity is also formed when no catalyst is used.

The same result is obtained when $NiCl_2$ is used instead of nickel tetracarbonyl.

What we claim is:

1. A process for the production methallyl phosphonic acid dialkyl esters of the formula

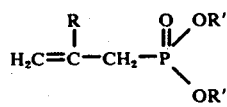

wherein
R represents hydrogen or methyl, and
R' represents a straight-chain or branched, unsubstituted or halogen-substituted alkyl radical having up to 4 carbon atoms, which comprises reacting allyl chloride or methallyl chloride with a phosphorous acid trialkyl ester (trialkyl phosphites) of the formula:

P (OR')$_3$ in which R' is as defined above, under atmospheric pressure at a temperature in the range of from 80° to 160° in the presence of from 0.5 to 7 mole % based on the phosphite of a catalyst selected from the group consisting of elemental nickel, Raney nickel, nickel tetracarbonyl, nickel triphenyl phosphine tricarbonyl, nickel-bis-(triphenyl phosphine)-dicarbonyl, π-allyl nickel chloride, π-allyl nickel bromide, π-allyl nickel iodide, π-cyclopentadienyl nickel nitrosyl, nickel diacrylonitrile, Raney cobalt, dicobalt octacarbonyl, cobalt-II-chloride and cobalt-II-bromide.

2. The process of claim 1, wherein said trialkyl phosphite and said catalyst are initially introduced either completely or in part under atmospheric pressure, the rest of the trialkyl phosphite and the allyl or methallyl chloride are then added and the alkyl chloride formed is distilled off from the reaction mixture.

3. The process of claim 1, wherein said catalyst is Raney nickel.

4. The process of claim 1, wherein said catalyst is nickel tetracarbonyl.

5. The process of claim 1, wherein said catalyst is π-allyl nickel chloride.

6. The process of claim 1, wherein said catalyst is Raney cobalt.

7. The process of claim 1, wherein said catalyst is dicobalt octacarbonyl.

8. The process of claim 1, wherein said catalyst is cobalt-II-chloride or cobalt-II-bromide.

* * * * *